United States Patent
Arimoto et al.

(10) Patent No.: US 6,294,578 B1
(45) Date of Patent: Sep. 25, 2001

(54) INSECTICIDES, MITICIDES AND METHOD FOR KILLING INSECTS AND MITES

(75) Inventors: Yutaka Arimoto, 1-16-15-203, Nobidome, Niza-shi, Saitama, 352-0011 (JP); Isamu Yamaguchi, Wako (JP)

(73) Assignees: The Institute of Physical and Chemical Research, Wako; Yutaka Arimoto, Niza, both of (JP)

( * ) Notice: Subject to any disclaimer, the term of this patent is extended or adjusted under 35 U.S.C. 154(b) by 0 days.

(21) Appl. No.: 09/035,996

(22) Filed: Mar. 6, 1998

(30) Foreign Application Priority Data

Mar. 7, 1997 (JP) .................................................. 9-053478

(51) Int. Cl.⁷ .............................. A01N 37/00; A01N 31/00
(52) U.S. Cl. .......................... 514/552; 514/506; 514/529; 514/546; 514/547; 514/549; 514/715; 514/722; 514/723; 514/724; 514/738; 514/739; 514/875; 514/975
(58) Field of Search ..................................... 514/506, 529, 514/546–552, 975, 875, 715, 722, 723, 724, 738, 739

(56) References Cited

U.S. PATENT DOCUMENTS

| | | | | |
|---|---|---|---|---|
| 2,357,077 | * | 8/1944 | Brown | 514/552 |
| 2,357,078 | * | 8/1944 | Brown | 514/547 |
| 2,374,918 | * | 5/1945 | Brown | 514/547 |
| 5,284,508 | * | 2/1994 | Shibata et al. | 106/267 |
| 5,912,208 | * | 6/1999 | Hioki et al. | 504/206 |

FOREIGN PATENT DOCUMENTS

| | | |
|---|---|---|
| 0 392 127 | 10/1990 | (EP) . |
| 55-167204 | * 12/1980 | (JP) . |
| 6-166602 | * 6/1994 | (JP) . |
| WO 95/34200 | 12/1995 | (WO) . |
| 96/03872 | * 2/1996 | (WO) . |
| 96/16539 | * 6/1996 | (WO) . |

OTHER PUBLICATIONS

Chemical Abstracts, vol. 119, No. 23, p. 325, AN 243596d, Dec. 6, 1993, JP 05 221 804, Aug. 31, 1993.

Noda et al., JP355167204A, Composition for controlling agricultural and horticultural blight and noxious insect (Dec. 1980), APS Messenger online, JPO & Japio file, Abstract.*

Kirk–Othmer, Encyclopedia of Chemical Technology, vol. 23, pp. 717–720, "Vegetable Oils," 1983.

* cited by examiner

*Primary Examiner*—Jose' G. Dees
*Assistant Examiner*—Frank Choi
(74) *Attorney, Agent, or Firm*—Oblon, Spivak, McClelland, Maier & Neustadt, P.C.

(57) ABSTRACT

An insecticidal and miticidal composition is provided which comprises at least one fatty acid ester selected from the group consisting of glycerin monooleate, glycerin monolinolate, glycerin monocaprylate, glycerin mono/dioleate, glycerin di/trioleate, glycerin mono/dilinolate, glycerin mono/diricinoleate, glycerin diacetomonolaurate, sorbitan laurate, sorbitan oleate, diglycerin laurate, diglycerin oleate, diglycerin monolaurate, diglycerin monooleate, tetraglycerin oleate, hexaglycerin laurate, decaglycerin laurate, propylene glycol monolaurate, and propylene glycol monooleate; and a nonionic surfactant. The insecticidal and miticidal composition does not have phytotoxicity but has satisfactory long lasting effects even if it is used in a lower concentration.

30 Claims, No Drawings

INSECTICIDES, MITICIDES AND METHOD FOR KILLING INSECTS AND MITES

FIELD OF THE INVENTION

This invention relates to an insecticidal and miticidal composition and a method for killing insects and mites.

BACKGROUND OF THE INVENTION

There have been used various compositions for control of insect pests such as mites such as spider mites, and aphids. For example, JP-A-55-57506 discloses a composition for control of insect pests which comprises a combination of sorbitan fatty acid ester or its ethylene oxide adduct and a water soluble polymer. However, the composition has disadvantage that it does not have satisfactory effects if it is used in a low concentration and the effects, if it is expressed, do not last long. Moreover, these mites and insect pests, in general, easily acquire tolerance to drug and therefore the insecticidal and miticidal effects fade away little by little.

SUMMARY OF THE INVENTION

Accordingly, an object of the present invention is to provide an insecticidal and miticidal composition which does not have phytotoxicity but has satisfactory effects even if it is used in a lower concentration and whose effects last long.

The present invention provides an insecticidal and miticidal composition which comprises at least one fatty acid ester selected from the group consisting of glycerin monooleate, glycerin monolinolate, glycerin monocaprylate, glycerin mono/dioleate (a mixture of glycerin monooleate and glycerin dioleate), glycerin di/trioleate (a mixture of glycerin dioleate and glycerin trioleate), glycerin mono/dilinolate (a mixture of glycerin monolinolate and glycerin dilinolate), glycerin mono/diricinoleate (a mixture of glycerin monoricinoleate and glycerin diricinoleate), glycerin diacetomonolaurate, sorbitan laurate, sorbitan oleate, diglycerin laurate, diglycerin oleate, diglycerin monolaurate, diglycerin monooleate, tetraglycerin oleate, hexaglycerin laurate, decaglycerin laurate, propylene glycol monolaurate, and propylene glycol monooleate; and a nonionic surfactant.

PREFERRED EMBODIMENTS OF THE INVENTION

The present invention is accomplished based on the discovery that a combination of a specific fatty acid ester and a nonionic surfactant has remarkably excellent insecticidal and miticidal effects as compared with a combination of other fatty acid ester and a nonionic surfactant.

The present invention provides a miticidal composition which comprises at least one fatty acid ester selected from the group consisting of glycerin monooleate, glycerin monolinolate, glycerin mono/diricinoleate, glycerin diacetomonolaurate, sorbitan laurate, diglycerin laurate, tetraglycerin oleate, propylene glycol monolaurate, and propylene glycol monooleate; and a nonionic surfactant.

Preferably, the miticidal composition of the present invention comprises at least one fatty acid ester selected from the group consisting of glycerin mono/diricinoleate, glycerin diacetomonolaurate, sorbitan laurate, diglycerin laurate, tetraglycerin oleate, and propylene glycol monolaurate; and a nonionic surfactant.

The present invention provides an insecticidal composition which comprises at least one fatty acid ester selected from the group consisting of glycerin monooleate, glycerin monolinolate, glycerin monocaprylate, glycerin mono/dioleate, glycerin di/trioleate, glycerin mono/dilinolate, glycerin mono/diricinoleate, glycerin diacetomonolaurate, sorbitan laurate, sorbitan oleate, diglycerin laurate, diglycerin oleate, diglycerin monolaurate, diglycerin monooleate, tetraglycerin oleate, hexaglycerin laurate, decaglycerin laurate, propylene glycol monolaurate, and propylene glycol monooleate; and a nonionic surfactant.

The present invention provides an aphicidal composition which comprises at least one fatty acid ester selected from the group consisting of glycerin monooleate, glycerin monocaprylate, glycerin mono/dioleate, glycerin di/trioleate, glycerin mono/dilinolate, glycerin mono/diricinoleate, glycerin diacetomonolaurate, sorbitan laurate, sorbitan oleate, diglycerin laurate, diglycerin oleate, diglycerin monolaurate, diglycerin monooleate, tetraglycerin oleate, hexaglycerin laurate, decaglycerin laurate, and propylene glycol monolaurate; and a nonionic surfactant.

Preferably, the aphicidal composition of the present invention comprises at least one fatty acid ester selected from the group consisting of glycerin diacetomonolaurate, sorbitan laurate, diglycerin laurate, glycerin mono/dioleate, hexaglycerin laurate, and propylene glycol monolaurate; and a nonionic surfactant.

The present invention provides a composition for killing greenhouse whitefly which comprises at least one fatty acid ester selected from the group consisting of glycerin monolinolate, glycerin monocaprylate, glycerin mono/dioleate, glycerin di/trioleate, glycerin mono/dilinolate, glycerin mono/diricinoleate, glycerin diacetomonolaurate, sorbitan laurate, sorbitan oleate, diglycerin laurate, diglycerin oleate, diglycerin monolaurate, diglycerin monooleate, tetraglycerin oleate, hexaglycerin laurate, decaglycerin laurate, propylene glycol monolaurate, and propylene glycol monooleate; and a nonionic surfactant.

Preferably, the composition for killing greenhouse whitefly of the present invention comprises at least one fatty acid ester selected from the group consisting of glycerin monolinolate, glycerin mono/dioleate, glycerin di/trioleate, glycerin mono/dilinolate, diglycerin monooleate, decaglycerin laurate, and propylene glycol monooleate; and a nonionic surfactant.

The present invention provides a composition for killing thrips which comprises at least one fatty acid ester selected from the group consisting of glycerin monolinolate, glycerin monocaprylate, glycerin mono/dioleate, glycerin di/trioleate, glycerin mono/dilinolate, glycerin mono/diricinoleate, glycerin diacetomonolaurate, sorbitan laurate, sorbitan oleate, diglycerin laurate, diglycerin oleate, diglycerin monolaurate, diglycerin monooleate, tetraglycerin oleate, hexaglycerin laurate, decaglycerin laurate, propylene glycol monolaurate, and propylene glycol monooleate; and a nonionic surfactant.

Preferably, the composition for killing thrips of the present invention comprises at least one fatty acid ester selected from the group consisting of glycerin diacetomonolaurate, glycerin monocaprylate, glycerin mono/dilinolate, sorbitan oleate, diglycerin oleate, and propylene glycol monooleate; and a nonionic surfactant.

Preferably, the nonionic surfactant used in the present invention is polyoxyethylene alkyl ether wherein the alkyl group has 6 to 24 carbon atoms, preferably 6 to 18 carbon atoms and the molar number of added ethylene oxide is 3 to 20, preferably 3 to 10.

In the composition of the present invention, the amount of the nonionic surfactant is preferably 1 to 40 parts by weight, more preferably 5 to 20 parts by weight, most preferably 8 to 10 parts by weight, per 100 parts by weight of the fatty acid ester.

The composition of the present invention preferably comprises a medium chain fatty acid triglyceride as an auxiliary agent for the preparation. The medium chain fatty acid triglyceride is very stable fats and oils and used in the field of lubricants and cosmetics. An alkyl group in the medium chain fatty acid triglycerides has preferably 7 to 11 carbon atoms. If the medium chain fatty acid triglyceride is used in the composition of the present invention, the amount thereof is preferably 1 to 40 parts by weight, more preferably 5 to 20 parts by weight and most preferably 5 to 10 parts by weight per 100 parts by weight of the fatty acid ester.

The composition of the present invention is spread directly on mites or insect pests present on the plants as it is, or after it is diluted with water or other solvent or carrier.

The concentration of the effective ingredients in the diluted liquid is preferably 0.02 to 10% by weight, more preferably 0.05 to 5% by weight, and most preferably 0.08 to 2% by weight. The amount to be spread (of the composition before diluted) varies depending on the adhesion of mites or insect pests but is generally in the range of from 0.5 to 20 kg/ha, preferably from 1 to 10 kg/ha, and more preferably 1.5 to 8 kg/ha.

For example, fatty acid ester and polyoxyethylene alkyl ether are mixed in the weight ratio of (99 to 70)/(1 to 30), for example 9/1 to prepare a composition of the present invention in the form of a liquid.

Alternatively, fatty acid ester, polyoxyethylene alkyl ether and diglycerin monooleate are mixed in the weight ratio of (94 to 80)/(3 to 10)/(3 to 10) to prepare a composition of the present invention in the form of liquid.

Further, fatty acid ester, polyoxyethylene alkyl ether, diglycerin monooleate and medium chain fatty acid triglyceride are mixed in the weight ratio of (95 to 70)/(2 to 10)/(2 to 10)/(1 to 10) to prepare a composition of the present invention in the form of a liquid, semi-fluid, paste or solid.

Examples of mites to which the composition of the present invention is applied to kill include spider mites such as two-spotted spider mite (*Tetranychus urticae Koch*), citrus red mite (*Panonychus citri McGregor*), European red mite (*Panonychus ulmi Koch*), clover spider mite (*Bryobia praetiosa Koch*), Kanzawa spider mite (*Tetranychus kanzawai Kishida*), yellow peach spider mite (*Tetranychus viennensis zacher*), carmine mite (*Tetranychus telarius Linne*), and Briwb mite (*Bryobia rubrioculus Scheuten*); citrus flat mite (*Brecipalupus lewisi McGregor*); rust mites such as Japanese citrus rust mite (*Aculus pelekassi Keifeer*), and grape rust mite (*Calepitrimerus vitis Nalepa*); common grain mite (*Tyrophagus putrescentiae Schrank*); ticks; and, house dust mites.

Examples of insect pests to which the composition of the present invention is applied to kill include aphids such as cotton aphid (*Aphis gossypii Glover*), cabbage aphid (*Brevicoryne brassicae Linne*) and green peach aphid (*Myzus persicae Sulzer*); louse such as whitefly; and thrips such as tea thrips (*Scitothrips dorsalis Hood*).

The present invention will be explained more in detail with reference to the following examples.

PREPARATION EXAMPLE 1

A fatty acid ester (9 parts by weight) and polyoxyethylene alkyl ether (1 part by weight) were mixed to prepare a composition of the present invention.

PREPARATION EXAMPLE 2

A fatty acid ester (8 parts by weight), polyoxyethylene alkyl ether (1 part by weight) and diglycerin monooleate (1 part by weight) were mixed to prepare a composition of the present invention.

PREPARATION EXAMPLE 3

A fatty acid ester (7 parts by weight), polyoxyethylene alkyl ether (1 part by weight), diglycerin monooleate (1 part by weight) and a medium chain fatty acid triglyceride (1 part by weight) were mixed to prepare a composition of the present invention.

The miticidal and insecticidal effects of the compositions of the present invention were evaluated according to the following methods.

Test Method 1

Mite (two-spotted spider mite)

① The mite is cultured on the seedling of kidney beans.

② Separately, seeds of kidney beans (variety: Paradise) are sowed and grown in an air-conditioned greenhouse.

③ Five seedlings are transplanted in a pot. Once true leaves come out, they are brought into contact with the seedlings of kidney beans on which the mite is cultured.

④ After they are contacted with each other for four days to confirm the transition of imago and larva and spawning, the drug solution diluted to a given concentration is sprayed on the leaves.

⑤ After the drug is sprayed, the plant is isolated and grown in a greenhouse at 20 to 25° C. and the number of living mites after two or three weeks is counted.

⑥ Miticidal rate is calculated according to the following equation. Miticidal rate (%)=100−(the number of living mites in treated division)/(the number of living mites in untreated division)×100

Test Method 2

Aphid (cotton aphid)

① Aphid is cultured on the seedlings of cucumber.

② Separately, seeds of cucumber (variety: Sagami Hanjiro) are sowed and grown in an air-conditioned greenhouse.

③ After true leaves come out, they are brought into contact with the seedlings of cucumber on which the aphid is cultured.

④ After they are contacted with each other for 4 to 7 days to confirm the breeding of the aphid on the new seedlings of cucumber, the drug solution diluted to a given concentration is sprayed on the leaves.

⑤ After the drug is sprayed, the plant is isolated and grown in a greenhouse at 20 to 25° C. and the number of living and dead aphid after one week is counted.

⑥ Insecticidal rate is calculated according to the following equation. Insecticidal rate (%)=(the number of dead aphid)/(the number of the total aphid)×100

Test Method 3

Whitefly

① Whitefly is cultured on the seedlings of tomato.

② Separately, seeds of tomato (variety: Momotarou) are sowed and grown in an air-conditioned greenhouse.

③ After two or three true leaves come out, they are brought into contact with the seedlings of tomato on which the whitefly is cultured.

④ After they are contacted with each other for 3 to 4 days to confirm the breeding of the whitefly on the new seedlings of tomato, the drug solution diluted to a given concentration is sprayed on the leaves.

⑤ After the drug is sprayed, the plant is isolated and grown in a greenhouse at 20 to 25° C. and the number of living whitefly after one week is counted.

⑥ Insecticidal rate is calculated according to the following equation. Insecticidal rate (%)=100−(the number of living whitefly in treated division)/(the number of living whitefly in untreated division)×100

Test Method 4

Thrips (Tea thrips)

① The thrips are cultured on the seedlings of cucumber.

② Separately, seeds of cucumber (variety: Sagami Hanjiro) are sowed and grown in an air-conditioned greenhouse.

③ After true leaves come out, they are brought into contact with the seedlings of cucumber on which the thrips are cultured.

④ After they are contacted with each other for 3 to 4 days to confirm the breeding of the thrips on the new seedlings of cucumber, the drug solution diluted to a given concentration is sprayed on the leaves.

⑤ After the drug is sprayed, the plant is isolated and grown in a greenhouse at 20 to 25° C. and the number of living thrips after one week is counted.

⑥ Insecticidal rate is calculated according to the following equation. Insecticidal rate (%)=100−(the number of living thrips in treated division)/(the number of living thrips in untreated division)×100

The miticidal or insecticidal effects of the compositions of the preparation examples obtained by the above methods are as follows.

Test Example 1
Fatty acid ester: propylene glycol monolaurate
Mite: Two-spotted spider mite

| Composition | Concentration (mg/100 ml) | Active ingredient (mg/100 ml) | Miticidal rate (%) |
|---|---|---|---|
| Preparation Ex. 1 | 100 | 90 | 95 |
| Preparation Ex. 2 | 100 | 90 | 98 |
| Preparation Ex. 3 | 100 | 80 | 100 |

Test Example 2
Fatty acid ester: Sorbitan laurate
Mite: Two-spotted spider mite

| Composition | Concentration (mg/100 ml) | Active ingredient (mg/100 ml) | Miticidal rate (%) |
|---|---|---|---|
| Preparation Ex. 1 | 100 | 90 | 78 |
| Preparation Ex. 2 | 100 | 90 | 83 |
| Preparation Ex. 3 | 100 | 80 | 87 |

Test Example 3
Fatty acid ester: Glycerin mono/diricinoleate
Mite: Two-spotted spider mite

| Composition | Concentration (mg/100 ml) | Active ingredient (mg/100 ml) | Miticidal rate (%) |
|---|---|---|---|
| Preparation Ex. 1 | 100 | 90 | 82 |
| Preparation Ex. 2 | 100 | 90 | 88 |
| Preparation Ex. 3 | 100 | 80 | 95 |

Test Example 4
Fatty acid ester: Glycerin diacetomonolaurate
Mite: Two-spotted spider mite

| Composition | Concentration (mg/100 ml) | Active ingredient (mg/100 ml) | Miticidal rate (%) |
|---|---|---|---|
| Preparation Ex. 1 | 100 | 90 | 80 |
| Preparation Ex. 2 | 100 | 90 | 84 |
| Preparation Ex. 3 | 100 | 80 | 96 |

Test Example 5
Fatty acid ester: Tetraglycerin oleate
Mite: Two-spotted spider mite

| Composition | Concentration (mg/100 ml) | Active ingredient (mg/100 ml) | Miticidal rate (%) |
|---|---|---|---|
| Preparation Ex. 1 | 100 | 90 | 93 |
| Preparation Ex. 2 | 100 | 90 | 96 |
| Preparation Ex. 3 | 100 | 80 | 99 |

Test Example 6
Fatty acid ester: Diglycerin laurate
Mite: Two-spotted spider mite

| Composition | Concentration (mg/100 ml) | Active ingredient (mg/100 ml) | Miticidal rate (%) |
|---|---|---|---|
| Preparation Ex. 1 | 100 | 90 | 93 |
| Preparation Ex. 2 | 100 | 90 | 96 |
| Preparation Ex. 3 | 100 | 80 | 99 |

Test Example 7
Fatty acid ester: Diglycerin laurate
Insect: Cotton aphid

| Composition | Concentration (mg/100 ml) | Active ingredient (mg/100 ml) | Insecticidal rate (%) |
|---|---|---|---|
| Preparation Ex. 1 | 200 | 180 | 82 |
| Preparation Ex. 2 | 200 | 180 | 95 |
| Preparation Ex. 3 | 200 | 160 | 100 |

Test Example 8
Fatty acid ester: Glycerin diacetomonolaurate
Insect: Cotton aphid

| Composition | Concentration (mg/100 ml) | Active ingredient (mg/100 ml) | Insecticidal rate (%) |
|---|---|---|---|
| Preparation Ex. 1 | 200 | 180 | 75 |
| Preparation Ex. 2 | 200 | 180 | 88 |
| Preparation Ex. 3 | 200 | 160 | 92 |

Test Example 9
Fatty acid ester: Glycerin mono/dioleate
Insect: Cotton aphid

| Composition | Concentration (mg/100 ml) | Active ingredient (mg/100 ml) | Insecticidal rate (%) |
|---|---|---|---|
| Preparation Ex. 1 | 200 | 180 | 85 |
| Preparation Ex. 2 | 200 | 180 | 87 |
| Preparation Ex. 3 | 200 | 160 | 98 |

Test Example 10
Fatty acid ester: Sorbitan laurate
Insect: Cotton aphid

| Composition | Concentration (mg/100 ml) | Active ingredient (mg/100 ml) | Insecticidal rate (%) |
|---|---|---|---|
| Preparation Ex. 1 | 200 | 180 | 81 |
| Preparation Ex. 2 | 200 | 180 | 86 |
| Preparation Ex. 3 | 200 | 160 | 96 |

Test Example 11
Fatty acid ester: Hexaglycerin laurate
Insect: Cotton aphid

| Composition | Concentration (mg/100 ml) | Active ingredient (mg/100 ml) | Insecticidal rate (%) |
|---|---|---|---|
| Preparation Ex. 1 | 200 | 180 | 77 |
| Preparation Ex. 2 | 200 | 180 | 82 |
| Preparation Ex. 3 | 200 | 160 | 90 |

Test Example 12
Fatty acid ester: propylene glycol monolaurate
Insect: Cotton aphid

| Composition | Concentration (mg/100 ml) | Active ingredient (mg/100 ml) | Insecticidal rate (%) |
|---|---|---|---|
| Preparation Ex. 1 | 200 | 180 | 85 |
| Preparation Ex. 2 | 200 | 180 | 92 |
| Preparation Ex. 3 | 200 | 160 | 97 |

Test Example 13
Fatty acid ester: Glycerin monoleate
Insect: Cotton aphid

| Composition | Concentration (mg/100 ml) | Active ingredient (mg/100 ml) | Insecticidal rate (%) |
|---|---|---|---|
| Preparation Ex. 1 | 200 | 180 | 84 |
| Preparation Ex. 2 | 200 | 180 | 87 |
| Preparation Ex. 3 | 200 | 160 | 91 |

Test Example 14
Fatty acid ester: Glycerin monolinolate
Insect: Whitefly

| Composition | Concentration (mg/100 ml) | Active ingredient (mg/100 ml) | Insecticidal rate (%) |
|---|---|---|---|
| Preparation Ex. 1 | 200 | 180 | 88 |
| Preparation Ex. 2 | 200 | 180 | 98 |
| Preparation Ex. 3 | 200 | 160 | 100 |

Test Example 15
Fatty acid ester: Glycerin mono/dioleate
Insect: Whitefly

| Composition | Concentration (mg/100 ml) | Active ingredient (mg/100 ml) | Insecticidal rate (%) |
|---|---|---|---|
| Preparation Ex. 1 | 200 | 180 | 86 |
| Preparation Ex. 2 | 200 | 180 | 94 |
| Preparation Ex. 3 | 200 | 160 | 100 |

Test Example 16
Fatty acid ester: Glycerin di/trioleate
Insect: Whitefly

| Composition | Concentration (mg/100 ml) | Active ingredient (mg/100 ml) | Insecticidal rate (%) |
|---|---|---|---|
| Preparation Ex. 1 | 200 | 180 | 75 |
| Preparation Ex. 2 | 200 | 180 | 87 |
| Preparation Ex. 3 | 200 | 160 | 93 |

Test Example 17
Fatty acid ester: Diglycerin monooleate
Insect: Whitefly

| Composition | Concentration (mg/100 ml) | Active ingredient (mg/100 ml) | Insecticidal rate (%) |
|---|---|---|---|
| Preparation Ex. 1 | 200 | 180 | 80 |
| Preparation Ex. 2 | 200 | 180 | 85 |
| Preparation Ex. 3 | 200 | 160 | 93 |

Test Example 18
Fatty acid ester: Decaglycerin laurate
Insect: Whitefly

| Composition | Concentration (mg/100 ml) | Active ingredient (mg/100 ml) | Insecticidal rate (%) |
|---|---|---|---|
| Preparation Ex. 1 | 200 | 180 | 89 |
| Preparation Ex. 2 | 200 | 180 | 94 |
| Preparation Ex. 3 | 200 | 160 | 99 |

Test Example 19
Fatty acid ester: propylene glycol monooleate
Insect: Whitefly

| Composition | Concentration (mg/100 ml) | Active ingredient (mg/100 ml) | Insecticidal rate (%) |
|---|---|---|---|
| Preparation Ex. 1 | 200 | 180 | 78 |
| Preparation Ex. 2 | 200 | 180 | 84 |
| Preparation Ex. 3 | 200 | 160 | 90 |

Test Example 20
Fatty acid ester: Diglycerin monolaurate
Insect: Whitefly

| Composition | Concentration (mg/100 ml) | Active ingredient (mg/100 ml) | Insecticidal rate (%) |
|---|---|---|---|
| Preparation Ex. 1 | 200 | 180 | 82 |
| Preparation Ex. 2 | 200 | 180 | 85 |
| Preparation Ex. 3 | 200 | 160 | 87 |

Test Example 21
Fatty acid ester: Glycerin monocaprylate
Insect: Thrips

| Composition | Concentration (mg/100 ml) | Active ingredient (mg/100 ml) | Insecticidal rate (%) |
|---|---|---|---|
| Preparation Ex. 1 | 200 | 180 | 92 |
| Preparation Ex. 2 | 200 | 180 | 97 |
| Preparation Ex. 3 | 200 | 160 | 100 |

Test Example 22
Fatty acid ester: Glycerin mono/dilinolate
Insect: Thrips

| Composition | Concentration (mg/100 ml) | Active ingredient (mg/100 ml) | Insecticidal rate (%) |
|---|---|---|---|
| Preparation Ex. 1 | 200 | 180 | 86 |
| Preparation Ex. 2 | 200 | 180 | 93 |
| Preparation Ex. 3 | 200 | 160 | 99 |

Test Example 23
Fatty acid ester: Glycerin diacetomonolaurate
Insect: Thrips

| Composition | Concentration (mg/100 ml) | Active ingredient (mg/100 ml) | Insecticidal rate (%) |
|---|---|---|---|
| Preparation Ex. 1 | 200 | 180 | 75 |
| Preparation Ex. 2 | 200 | 180 | 88 |
| Preparation Ex. 3 | 200 | 160 | 91 |

Test Example 24
Fatty acid ester: Sorbitan oleate
Insect: Thrips

| Composition | Concentration (mg/100 ml) | Active ingredient (mg/100 ml) | Insecticidal rate (%) |
|---|---|---|---|
| Preparation Ex. 1 | 200 | 180 | 84 |
| Preparation Ex. 2 | 200 | 180 | 91 |
| Preparation Ex. 3 | 200 | 160 | 95 |

Test Example 25
Fatty acid ester: Diglycerin oleate
Insect: Thrips

| Composition | Concentration (mg/100 ml) | Active ingredient (mg/100 ml) | Insecticidal rate (%) |
|---|---|---|---|
| Preparation Ex. 1 | 200 | 180 | 77 |
| Preparation Ex. 2 | 200 | 180 | 87 |
| Preparation Ex. 3 | 200 | 160 | 89 |

Test Example 26
Fatty acid ester: propylene glycol monooleate
Insect: Thrips

| Composition | Concentration (mg/100 ml) | Active ingredient (mg/100 ml) | Insecticidal rate (%) |
|---|---|---|---|
| Preparation Ex. 1 | 200 | 180 | 89 |
| Preparation Ex. 2 | 200 | 180 | 88 |
| Preparation Ex. 3 | 200 | 160 | 91 |

The fatty acid esters, polyoxyethylene alkyl ether and medium chain fatty acid triglyceride used in the above examples are all commercially available from Riken Vitamin Co., Ltd. under the following trade names.

Polyoxyethylene alkyl ether: Rikemal B-205 (HLB=12.0; the molar number of added ethylene oxide=5 moles; fatty acid ester: carbon number 12=50 mole %, carbon number 13=50 mole %)

Medium chain fatty acid triglyceride: Actor M-1, fatty acid ester: carbon number 8=60 mole %, carbon number 10=40 mole %, clouding point=−6° C.~−7° C.)

Fatty acid esters:

Test Example 1: propylene glycol monolaurate; Rikemal PL-100

Test Example 2: sorbitan laurate; Rikemal L-250A

Test Example 3: glycerin mono/diricinoleate; Rikemal R-200

Test Example 4: glycerin diacetomonolaurate; Poem G-002

Test Example 5: tetraglycerin oleate; Poem J-4581
Test Example 6: diglycerin laurate; Rikemal L-71-D
Test Example 7: diglycerin laurate; Rikemal L-71-D
Test Example 8: glycerin diacetomonolaurate; Poem G-002
Test Example 9: glycerin mono/dioleate; Rikemal OL-200
Test Example 10: sorbitan laurate; Rikemal L-250A
Test Example 11: hexaglycerin laurate; Poem J-6021
Test Example 12: propylene glycol monolaurate; Rikemal PL-100
Test Example 13: glycerin monooleate; Rikemal OL-100
Test Example 14: glycerin monolinolate; Rikemal MU-100
Test Example 15: glycerin mono/dioleate; Rikemal OL-200
Test Example 16: glycerin di/trioleate; Rikemal OL-95
Test Example 17: diglycerin monooleate; Rikemal DO-100
Test Example 18: decaglycerin laurate; Poem J-0021
Test Example 19: propylene glycol monooleate; Rikemal PO-100
Test Example 20: diglycerin monolaurate; Rikemal DL-100
Test Example 21: glycerin monocaprylate; Poem M-100
Test Example 22: glycerin mono/dilinolate; Rikemal CS-200
Test Example 23: glycerin diacetomonolaurate; Poem G-002
Test Example 24: sorbitan oleate; Rikemal O-80
Test Example 25: diglycerin oleate; Rikemal O-71-D(E)
Test Example 26: propylene glycol monooleate; Rikemal PO-100

What is claimed is:

1. A nonphytotoxic insecticidal or miticidal composition, comprising:
   (i) diglycerin monooleate;
   (ii) at least one fatty acid ester selected from the group consisting of glycerin mono/diricinoleate and propylene glycol monolaurate; and
   (iii) a polyoxyethylene alkyl ether,
   wherein the weight ratio of (i) to (ii) to (iii) is (2 to 10)/(95 to 70)/(2 to 10).

2. The composition of claim 1, wherein the weight ratio of (i) to (ii) to (iii) is (3 to 10)/(94 to 80)/(3 to 10).

3. The composition of claim 1, wherein (ii) is glycerin mono/diricinoleate.

4. The composition of claim 1, wherein (ii) is propylene glycol monolaurate.

5. The composition of claim 1, further comprising a medium chain fatty acid triglyceride.

6. The composition of claim 5, which contains 1 to 40 parts by weight of the medium chain fatty acid triglyceride per 100 parts by weight of the fatty acid ester.

7. The composition of claim 5, which contains 5 to 20 parts by weight of the medium chain fatty acid triglyceride per 100 parts by weight of the fatty acid ester.

8. The composition of claim 5, which contains 5 to 10 parts by weight of the medium chain fatty acid triglyceride per 100 parts by weight of the fatty acid ester.

9. The composition of claim 5, wherein the alkyl group in the fatty acid triglyceride has 7 to 11 carbon atoms.

10. The composition of claim 1, wherein the alkyl group of the polyoxyethylene alkyl ether has 6 to 24 carbon atoms.

11. A nonphytotoxic aphicidal composition, comprising:
    (i) diglycerin monooleate;
    (ii) at least one fatty acid ester selected from the group consisting of glycerin mono/diricinoleate and propylene glycol monolaurate; and
    (iii) a polyoxyethylene alkyl ether,
    wherein the weight ratio of (i) to (ii) to (iii) is (2 to 10)/(95 to 70)/(2 to 10).

12. The composition of claim 11, wherein the weight ratio of (i) to (ii) to (iii) is (3 to 10)/(94 to 80)/(3 to 10).

13. The composition of claim 11, wherein (ii) is glycerin mono/diricinoleate.

14. The composition of claim 11, wherein (ii) is propylene glycol monolaurate.

15. The composition of claim 11, further comprising a medium chain fatty acid triglyceride.

16. The composition of claim 15, which contains 1 to 40 parts by weight of the medium chain fatty acid triglyceride per 100 parts by weight of the fatty acid ester.

17. The composition of claim 15, which contains 5 to 20 parts by weight of the medium chain fatty acid triglyceride per 100 parts by weight of the fatty acid ester.

18. The composition of claim 15, which contains 5 to 10 parts by weight of the medium chain fatty acid triglyceride per 100 parts by weight of the fatty acid ester.

19. The composition of claim 15, wherein the alkyl group in the fatty acid triglyceride has 7 to 11 carbon atoms.

20. The composition of claim 11, wherein the alkyl group of the polyoxyethylene alkyl ether has 6 to 24 carbon atoms.

21. A nonphytotoxic composition for killing greenhouse whitefly or thrips, comprising:
    (i) diglycerin monooleate;
    (ii) at least one fatty acid ester selected from the group consisting of glycerin mono/diricinoleate and propylene glycol monolaurate; and
    (iii) a polyoxyethylene alkyl ether,
    wherein the weight ratio of (i) to (ii) to (iii) is (2 to 10)/(95 to 70)/(2 to 10).

22. The composition of claim 21, wherein the weight ratio of (i) to (ii) to (iii) is (3 to 10)/(94 to 80)/(3 to 10).

23. The composition of claim 21, wherein (ii) is glycerin mono/diricinoleate.

24. The composition of claim 21, wherein (ii) is propylene glycol monolaurate.

25. The composition of claim 21, further comprising a medium chain fatty acid triglyceride.

26. The composition of claim 25, which contains 1 to 40 parts by weight of the medium chain fatty acid triglyceride per 100 parts by weight of the fatty acid ester.

27. The composition of claim 25, which contains 5 to 20 parts by weight of the medium chain fatty acid triglyceride per 100 parts by weight of the fatty acid ester.

28. The composition of claim 25, which contains 5 to 10 parts by weight of the medium chain fatty acid triglyceride per 100 parts by weight of the fatty acid ester.

29. The composition of claim 25, wherein the alkyl group in the fatty acid triglyceride has 7 to 11 carbon atoms.

30. The composition of claim 21, wherein the alkyl group of the polyoxyethylene alkyl ether has 6 to 24 carbon atoms.

* * * * *